US006764842B2

(12) United States Patent
Sturr et al.

(10) Patent No.: US 6,764,842 B2
(45) Date of Patent: Jul. 20, 2004

(54) ENANTIOSELECTIVE BIOREDUCTION FOR THE PREPARATION OF INTEGRIN RECEPTOR ANTAGONIST INTERMEDIATES

(75) Inventors: Michael G. Sturr, Mountainside, NJ (US); Russell Fieldon Boyd, Robbinsville, NJ (US); Kodzo Gbewonyo, Somerset, NJ (US); Joseph Nti-Gyabaah, Somerset, NJ (US); David J. Pollard, Monroe Township, NJ (US); James Christopher McWilliams, Basking Ridge, NJ (US); Kathleen A. Telari, New York, NY (US)

(73) Assignee: Merck & Co., Inc., Rahway, NJ (US)

(*) Notice: Subject to any disclaimer, the term of this patent is extended or adjusted under 35 U.S.C. 154(b) by 28 days.

(21) Appl. No.: 10/107,889

(22) Filed: Mar. 27, 2002

(65) Prior Publication Data

US 2002/0187988 A1 Dec. 12, 2002

Related U.S. Application Data

(60) Provisional application No. 60/279,384, filed on Mar. 28, 2001.

(51) Int. Cl.[7] .......................... C12P 17/18; C12N 1/16
(52) U.S. Cl. ................................. 435/119; 435/255.4
(58) Field of Search ........................ 435/119, 255.4

(56) References Cited

U.S. PATENT DOCUMENTS 6,048,861 A   4/2000   Askew et al.

FOREIGN PATENT DOCUMENTS

WO        WO 99/31061        6/1999

OTHER PUBLICATIONS

Kawai, et al., "Asymmetric Reduction of Alpha, Beta–Unsaturated Ketones with a Carbon–Carbon Double–Bond Reductase from Baker's Yeast", Tetrahedron Letters 39, pp. 5225–5228 (1998).
Suga, et al., "Selective Hydrogenation of the C–C Double Bond Of Alpha, Beta Unsaturated Carbonyl Compounds by the Immobilized Cells of *Nicotiana tabacum*", Journal of Natural Products, vol. 56, No. 8, pp. 1406–1409 (1993).
Hage, et al., "Asymmetric reduction of ketones via whole cell bioconversions and transfer hydrogenation: complementary approaches", Tetrahedron: Asymmetry 12, pp. 1025–1034 (2001).

Chartrain, et al., "Asymmetric Bioreduction of Benzyl Acetoacetate to its Corresponding Alcohol, Benzyl (S)–(+) 3 Hydroxybutyrate by the Yeast *Candida schatavii* MY1831", Journal of Fermentation Bioengineering, vol. 82, No. 5, pp. 507–508 (1996).

Chartrain, et al., "Asymmetric Bioreduction of Cyclohexylphenyl Ketone to Its Corresponding Alcohol (+)–Cyclohexylphenyl Alcohol by the Yeast *Candida magnoliae* My1785", Journal of Fermentation Bioengineering, vol. 83, No. 4, pp. 395–396, (1997).

Ushio, et al., "Selective inhibition of R–enzymes by simple organic acids in yeast catalyzed reduction of ethyl 3 oxobutanoate", Enzyme Microb. Technol., vol. 13, pp. 834–839, (1991).

Chartrain, et al. "Asymmetric Bioreduction of (2–(4–nitro–phenyl)–N–(2–oxo–2–pryidin–3–yl–ethyl)–acetamide) to its corresponding (R) alcohol [(R)–N–(2–hydroxy–2–pyridin–3–yl–ethyl)–2–(4–nitro–phenyl)–acetamide] by using *Candida sorbophila* MY 1833", Enzyme and Microbial & Microbial Technology, vol. 25, pp. 489–496 (1999).

Kawai, et al., "Stereochemical Control in Microbial Reduction XXVIII. Asymmetric Reduction of Alpha, Beta Unsaturated Ketones with Bakers' Yeast", Bull. Chem. Soc. Jpn., vol. 69, pp. 2633–2638 (1996).

*Primary Examiner*—Hebert J. Lilling
(74) *Attorney, Agent, or Firm*—Patricia A. Shatynski; Melvin Winokur

(57) ABSTRACT

The present invention relates to a novel enantioselective bioreduction using a yeast microorganism for the preparation of the chiral allylic alcohols of structural formula I (R is hydrogen or methyl) which are useful in the asymmetric synthesis of integrin αvβ3 receptor antagonists.

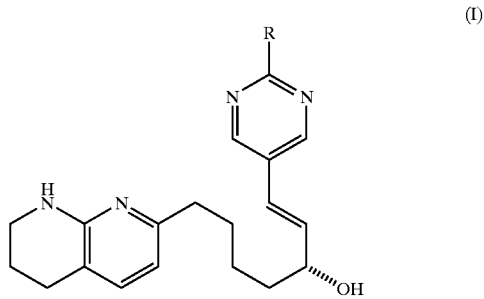

(I)

8 Claims, No Drawings

ENANTIOSELECTIVE BIOREDUCTION FOR THE PREPARATION OF INTEGRIN RECEPTOR ANTAGONIST INTERMEDIATES

This application claims the benefit of provisional application No. 60/279,384, filed Mar. 28, 2001.

FIELD OF THE INVENTION

The present invention relates to a bioreductive process for the efficient preparation of chiral allylic alcohol intermediates which are useful in the asymmetric synthesis of integrin αvβ3 receptor antagonists. The process comprises an enantioselective 1,2-reduction of a prochiral α,β-unsaturated ketone using a yeast microorganism to afford a chiral allylic alcohol which can be further processed into the desired substituted nonanoic acid derivative, which is useful as an integrin αvβ3 receptor antagonist for the inhibition of bone resorption and treatment of osteoporosis.

BACKGROUND OF THE INVENTION

The present invention provides an efficient process for the preparation of a chiral allylic alcohol of structural formula I,

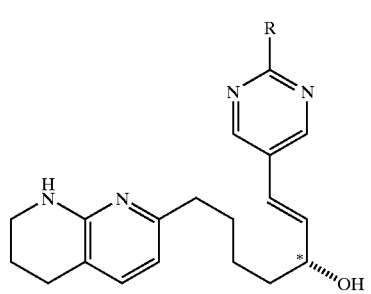

having the (R)-configuration at the stereogenic center marked with an *; wherein R is hydrogen or methyl.

The preparation of compounds of structural formula I in the racemic form was disclosed in U.S. Pat. No. 6,048,861 (Apr. 11, 2000), which is incorporated by reference herein in its entirety. The racemic allylic alcohols disclosed therein were converted in several steps into the desired 3-(pyrimidin-5-yl)- and 3-(2-methyl-pyrimidin-5-yl)-9-(5,6,7,8-tetrahydro-[1,8]-naphthyridin-2-yl)-nonanoic acids, which are useful as integrin αvβ3 receptor antagonists for the inhibition of bone resorption. The enantiomerically pure forms of the final product were obtained by means of HPLC resolution of the racemic mixture on a chiral solid support. Since only one antipode of the final product is preferred for use as an integrin αvβ3 receptor antagonist, the achiral process disclosed in U.S. Pat. No. 6,048,861 is inefficient in the sense that equal amounts of the less preferred enantiomer are obtained.

The present invention provides a process for the preparation of a chiral allylic alcohol of structural formula I having the (R)-configuration at the indicated stereogenic center in an efficient enantioselective fashion via bioreduction of a prochiral α,β-unsaturated ketone of structural formula II with a yeast microorganism.

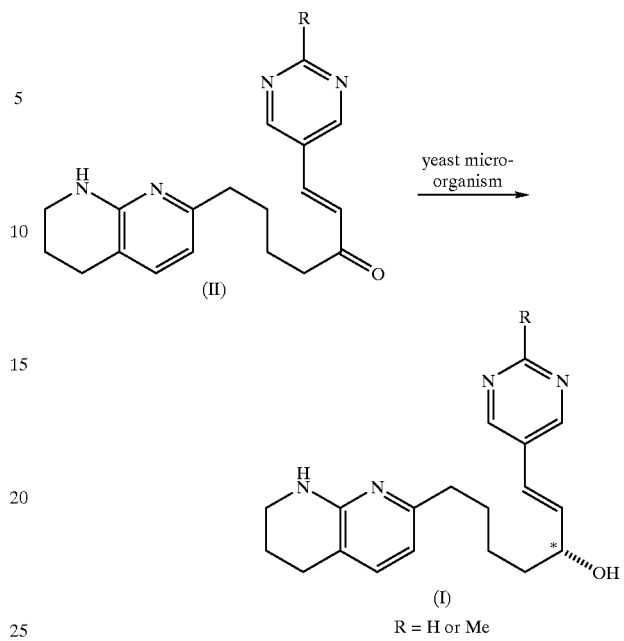

SUMMARY OF THE INVENTION

The present invention is concerned with a process for the preparation of chiral (R)-allylic alcohols of structural formula I. The process utilizes an enantioselective bioreduction with a yeast microorganism under propagation conditions that give rise to enhanced enantioselectivity in the reduction of a prochiral α,β-unsaturated ketone of structural formula II. The chiral (R)-allylic alcohols obtained in this fashion are key intermediates in the asymmetric synthesis of integrin αvβ3 receptor antagonists, which are useful for inhibiting bone resorption and treating osteoporosis.

DETAILED DESCRIPTION OF THE INVENTION

The process of the present invention involves the preparation of a chiral allylic alcohol of structural formula I having the (R)-configuration at the indicated stereogenic center by an asymmetric bioreduction reaction involving the incubation of an enone substrate of structural formula II with whole cells of a yeast microorganism in a suitable propagation medium.

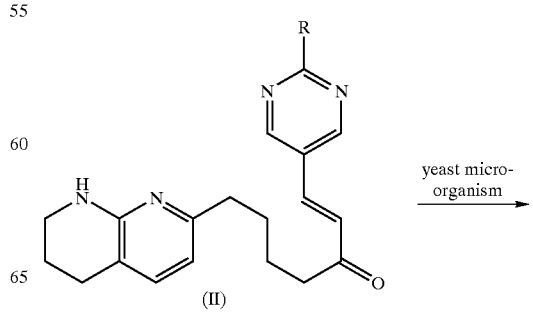

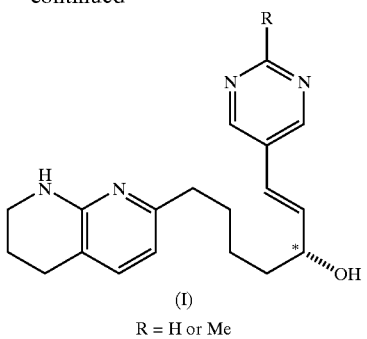

(I)

R = H or Me

The chiral allylic alcohols of structural formula I of the present invention can be converted in a 3-step sequence of Claisen rearrangement, hydrogenation, and hydrolysis, as described in U.S. Pat. No. 6,048,861, into the final products of structural formula III, which are useful as integrin αvβ3 receptor antagonists.

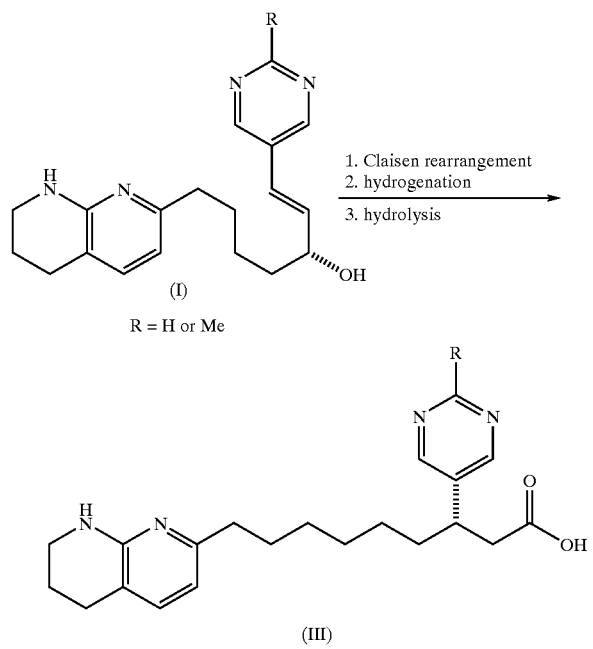

Prior to to filing date of the present application, samples of the microorganisms, *Candida chilensis* strain MY1708 and *Candida schatavii* strain MY1831, were deposited at the American Type Culture Collection (ATCC), Manassass, Va. The culture assess designations are ATCC PTA-4078 and 74439, respectively. The deposits will be maintained in the ATCC under the terms of the Budapest Treaty on the International Recognition of the Deposit of Microorganisms for the Purposes of Patent Procedure. Upon granting of a patent disclosing the deposits, all restrictions imposed by the depositor on the availability to the public of the deposited material will be irrevocably removed.

The full taxonomic profiles of *Candida chilensis* and *Candida schatavii* are detailed in: The Yeasts, A taxonomic study 4th edition (Editors Kurtzman and Fell 1998 Elsevier). The following is a brief description of growth, morphological and taxonomic characteristics of *Candida chilensis* and *Candida schatavii*.

(a) *Candida chilensis* strain MY 1708 could be propagated on complex growth media including Saboraud Dextrose Broth (SDB, Difco), Yeast Extract/Peptone, and Potato Dextrose Broth. Galactose, glycerol, and glucose were demonstrated to be assimilated carbon sources and either glutamate or ammonium could satisfy nitrogen source requirement when defined yeast basal media were employed. Fermentative growth was possible only with glucose as a carbon source. Growth on SDB agar plates at 25 C. was apparent within 48 hours. Growth at 29 C. was sluggish and no growth at 35 C. could be observed. Colonies were smooth, white to beige, and irregular at edges. Microscopic evaluation indicated ovoidal to longer elliptical forms (average approximately 4 by 4 uM) typically as single units but with some tendency to cluster.

(b) *Candida schatavii* strain MY1831 could also be propagated on the complex growth media described above for *Candida chilensis*. Galactose, glycerol, and glucose also served as carbon sources and glutamate or ammonium could be utilized as carbon source. Either glucose or galactose could be used as carbon source to support fermentative growth. Colony formation was evident on SDB medium within 48 hours at 25 C., 29 C., and in contrast to *Candida chilensis*, 35 C. Colonies were white to cream and shiny. Ovoid to elliptical morphology (average 4 by 4 uM, similar to chilensis) was observed microscopically typically as single cells or in small clusters (<3).

In one embodiment of the enantioselective bioreduction of the present invention, the yeast microorganism is *Candida chilensis* strain MY1708 or *Candida schatavii* strain MY1831. In a class of this embodiment, the yeast microorganism is *Candida chilensis* strain MY1708.

The bioreduction requires growth of the microorganism, such as *Candida chilensis* or *Candida schatavii*, in the presence of a suitable propagation medium, such as Yeast media (YM), Sabouraud dextrose broth (SDB), and Yeast nitrogen base (YNB), or a yeast medium as defined in Table 1, for 24–96 hours followed by a period of contact with the ketone substrate (I) under appropriate incubation conditions. The presence of the allylic alcohol product is observed postcharge when solvent-extracted samples are analyzed by reverse-phase high-performance liquid chromatography (RP-HPLC). In a second embodiment, the enone substrate of formula II is supplied at a final concentration of 0.5 to 15 grams per liter. The incubation conditions consist of aeration at a temperature of about 22° C. to about 30° C. at a pH of about 6.5 to about 8.5, and about 5–50 g/L of glucose to regenerate the required cofactor in whole cells.

In another embodiment, the bioreduction of the present invention is carried out in the presence of a carboxylic acid of structural formula IV:

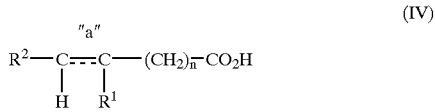

wherein

"a" represents a single bond or a double bond;

n is 0, 1, or 2;

$R^1$ is hydrogen, phenyl, or methyl; and $R^2$ is $C_{1-4}$ alkyl or aryl wherein aryl is selected from the group consisting of phenyl, naphthyl, biphenyl, pyridyl, furanyl, thienyl, pyrrolyl, benzofuranyl, benzothiophenyl, and indolyl, wherein the aryl group is unsubstituted or substituted with one to five substituents independently selected from halogen, amino, $C_{1-4}$ alkylamino, di-($C_{1-4}$ alkyl)amino, hydroxy, $C_{1-4}$ alkoxy, and $C_{1-4}$ alkyl. When "a" represents a double bond, both the "cis" and "trans" geometric isomers are intended to be encompassed within the carboxylic acids of formula IV.

In one class of this embodiment, "a" represents a double bond, n is 0, $R^1$ is hydrogen, and $R^2$ is aryl. In a subclass of this class, $R^2$ is phenyl unsubstituted or substituted with one to two substituents independently selected from halogen, amino, methyl, and methoxy. A specific embodiment is trans-cinnamic acid. In another class of this embodiment, the carboxylic acid of formula IV is added in an amount of about 1 to about 50 molar equivalents of the enone substrate of formula II.

The addition of a carboxylic acid of formula IV to the fermentation mixture affords lower amounts of the saturated alcohol of formula V and saturated ketone of structural formula VI and an increase in the enantioselectivity of the bioreduction.

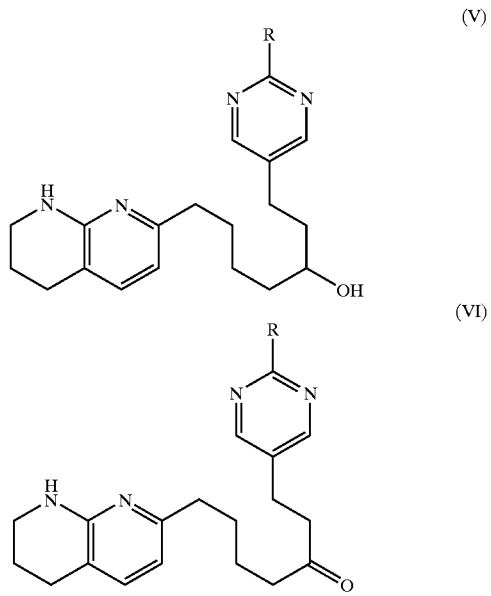

(V)

(VI)

The term "% enantiomeric excess" (abbreviated "ee") shall mean the % major enantiomer less the % minor enantiomer. Thus, an 80% enantiomeric excess corresponds to formation of 90% of one enantiomer and 10% of the other. The term "enantiomeric excess" is synonymous with the term "optical purity."

The term "enantioselective" shall mean a reaction in which one enantiomer is produced (or destroyed) more rapidly than the other, resulting in the predominance of the favored enantiomer in the mixture of products.

Microorganism *Candida chilensis* Strain MY1708 (ATCC PTA-4078)

A biologically pure sample of *Candida chilensis* strain MY1708 is currently available under the Budapest Treaty in the permanent culture collection of the American Type Culture Collection, 12301 Parklawn Drive in Rockville, Md. 20852, from which it is available under the Accession Number ATCC PTA-4078.

Microorganism *Candida schatavii* Strain MY1831 (ATCC 74439)

A biologically pure sample of *Candida schatavii* strain MY1831 is currently available under the Budapest Treaty in the permanent culture collection of the American Type Culture Collection, 12301 Parklawn Drive in Rockville, Md., from which it is available under the Accession Number ATCC 74439.

The following Examples illustrates the preparation of the compounds of formula I and as such are not to be considered as limiting the invention set forth in the claims appended thereto.

EXAMPLE 1

Reduction of Enone 2 Mediated by *Candida Chilensis* Strain MY1708

Step A: Preparation of 2-methyl-pyrimidine-5-carboxaldehyde (6)

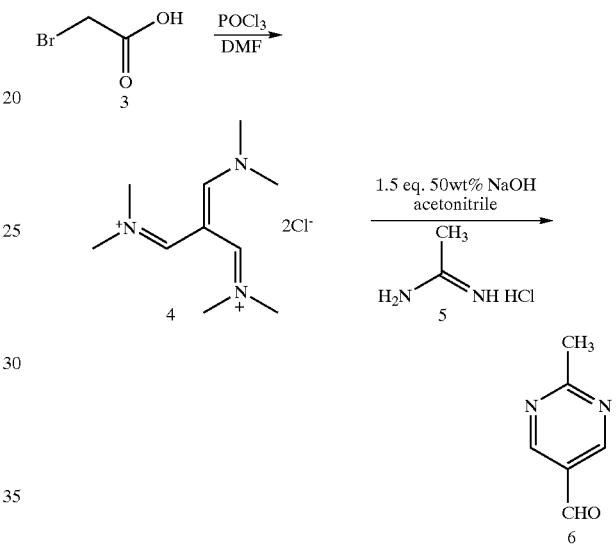

To a solution of bromoacetic acid 3 (12 g, 86.4 mmol) in DMF (44 mL) at 90° C. was added phosphorous oxychloride (24 mL, 260 mmol) over 5 h and then heated to 110° C. After stirring at 110° C. for 2.5 h, the mixture was cooled to 45° C. and quenched into cold isopropanol (44 mL) at 2° C. and diluted with isopropyl acetate (44 mL) and then treated with water (6.2 mL), which was added over 45 minutes at 2° C. to form the dichloride vinamidinium salt 4. After stirring for 1 h, the deposited solid was collected and washed with isopropyl acetate (2×14 mL) and acetonitrile (2×14 mL) to afford 4 (12.0 g) as pale yellow crystals.

To a slurry mixture of dichloride vinamidinium salt 4 (10.1 g, 39.9 mmole) and acetamidine hydrochloride 5 (4.2 g, 44.4 mmol) in acetonitrile (48 mL) at 22° C. was added 50% sodium hydroxide (4.9 g, 61.1 mmol) over 1.5 h and stirred at room temperature for 1.5 h.

The reaction mixture was filtered and washed with acetonitrile (10 mL), and the combined filtrate was concentrated under reduced pressure and solvent switched to heptane. The resulting heptane slurry mixture of crude 6 (25 mL) was extracted with methyl t-butyl ether (MTBE) (4×20 mL) at 40° C. The combined MTBE extract was filtered through a pad of fine silica gel and concentrated under reduced pressure. The residue was recrystallized from heptane to give aldehyde 6 (2.15 g) as pale yellow solid; m.p. 78–79° C.

$^1$H NMR (400 MHz, CDCl$_3$): δ 10.09 (s, 1H), 9.03 (s, 2H), 2.79 (s, 3H) ppm.

$^{13}$C NMR (100 MHz, CDCl$_3$): δ 189.0, 173.2, 158.2, 126.3, 26.7 ppm.

Step B: 1-(2-Methylpyrimidin-5-yl)-7-(5,6,7,8-tetrahydro-[1,8]naphthyridin-2-yl)-hept-1-en-3-one (2)

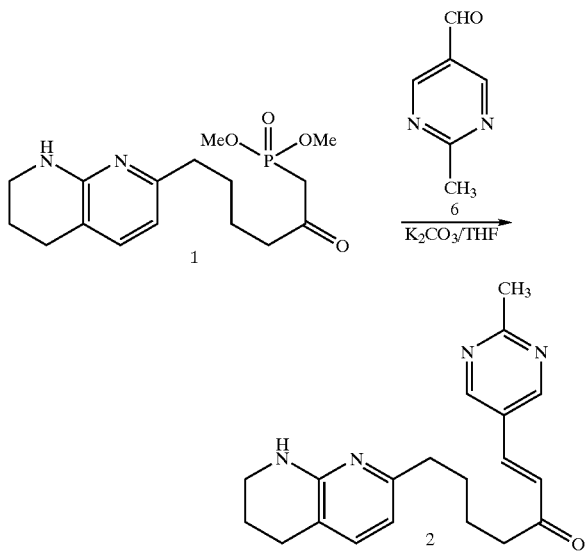

A stirred suspension of anhydrous powdered $K_2CO_3$ (6.21 g, 45 mmol), ketophosphonate 1 (for preparation of 1, see U.S. Pat. No. 6,048,861) (7.66 g, 22.5 mmol), and 2-methyl-pyrimidine-5-carboxaldehyde 6 (2.5 g, 20.5 mmol) in THF (250 mL) was heated at reflux for 4 h. After cooling to room temperature, the mixture was diluted with EtOAc (500 mL) and washed with water (100 mL) and brine (100 mL). The organic solution was dried over $MgSO_4$, filtered and concentrated. The residue was purified by flash chromatography ($SiO_2$; 10% $EtOH/CH_2Cl_2$) to give 5.7 g of the enone adduct 2 as a tan solid.

$^1$H NMR (400 MHz, $CDCl_3$): δ 8.77 (s, 2H), 7.42 (d, J=16.3 Hz, 1H), 7.04 (d, J=7.3 Hz, 1H), 6.80 (d, J=16.3 Hz, 1H), 6.34 (d, J=7.3 Hz, 1H) 4.80 (br s, 1H), 3.38 (m, 2H), 2.76 (s, 3H), 2.70–2.65 (om, 4H), 2.57 (m, 2H), 1.88 (m, 2H), 1.74–1.70 (om, 4H) ppm. $^{13}$C NMR (100 MHz, $CDCl_3$): δ 199.5, 169.4, 158.0, 156.0, 155.9, 136.8, 135.1, 128.4, 125.5, 113.4, 111.5, 41.8, 41.4, 37.7, 29.5, 26.5, 26.2, 24.0, 21.6 ppm.

Step C: (R)-1-(2-Methyl-pyrimidin-5-yl)-7-(5,6,7,8-tetrahydro-[1,8]-Naphthyridin-2-yl)-hept-1-en-3-ol (7)

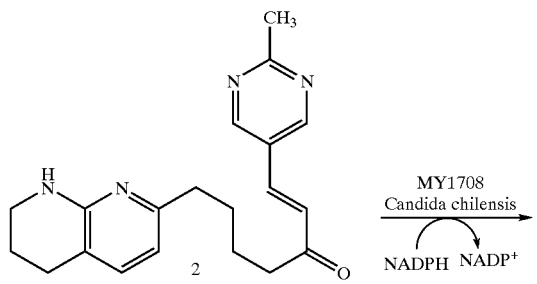

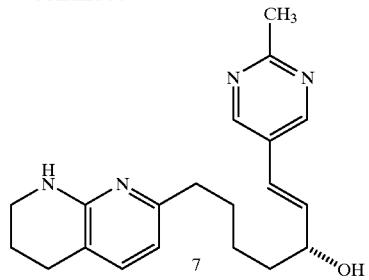

Bioreduction

Step 1: Cell growth—The yeast medium used for the fermentation process is shown in Table 1 above. The fermenter was sterilized (121° C. for 45 min) containing the potassium phosphate monobasic, sodium phosphate dibasic, magnesium sulfate heptahydrate, calcium carbonate, and monosodium glutamate, as well as trace elements. Glucose was added to the fermenter after separate sterilization. The vitamins were filter-sterilized to the post sterile fermenter. *Candida chilensis* yeast cells (MY1708) were inoculated into the fermenter at around 0.04–1% v/v from a frozen source. The temperature was maintained at 25° C. and the pH at 4.5 using 25% v/v sulfuric acid and 25% w/v sodium hydroxide. A glucose feed (2 g/Lh) was started when glucose consumption is near completion (20–30 h). The fermentation was completed at 30–50 hours.

TABLE 1

Defined yeast medium used for bioconversion

| | | |
|---|---|---|
| D-Biotin | 4.4–17.65 | Micrograms/Liter |
| Calcium Pantothenate | 5650–7059 | Micrograms/Liter |
| Folic Acid | 14–17.7 | Micrograms/Liter |
| myo-Inositol | 1400–17647 | Micrograms/Liter |
| Niacin (Nicotinic Acid) | 2820–3529 | Micrograms/Liter |
| p-Aminobenzoic Acid | 1400–1765 | Micrograms/Liter |
| Pyridoxine Hydrochloride | 2823–3529 | Micrograms/Liter |
| Thiamine Hydrochloride | 882–3529 | Micrograms/Liter |
| Riboflavin | 1400–1765 | Micrograms/Liter |
| Boric Acid | 1103–4411.8 | Micrograms/Liter |
| Copper Sulfate Pentahydrate | 138–552.3 | Micrograms/Liter |
| Potassium Iodide | 705–882 | Micrograms/Liter |
| Ferric Chloride Hexahydrate | 1400–1764 | Micrograms/Liter |
| Manganese Sulfate Monohydrate | 3500–4485 | Micrograms/Liter |
| Sodium Molybdate Dihydrate | 1500–1907 | Micrograms/Liter |
| Zinc Sulfate Heptahydrate | 3141–6282 | Micrograms/Liter |
| L-Histidine Monohydrochioride | 8–10 | Milligram/Liter |
| LD-Methionine | 16–20 | Milligram/Liter |
| LD-Tryptophan | 16–20 | Milligram/Liter |
| Potassium Phosphate Monobasic | 7–8.82 | grams/Liter |
| Magnesium Sulfate Heptahydrate | 3–9 | grams/Liter |
| Sodium Phosphate Dibasic | 0.8–1.07 | grams/Liter |
| Calcium Carbonate | 0.3–0.8 | grams/Liter |
| MonoSodium Glutamate | 18–32 | grams/Liter |
| Polypropylene Glycol, P-2000 | 0.5 | Milliliters/Liter |
| Glucose Monohydrate | 20–40 | grams/Liter |

Step 2: Bioreaction—For the bioconversion, the pH was increased to 8.0 via addition of 25% w/v sodium hydroxide. This was followed by a 10 g/L glucose addition and finally the substrate. Substrate (100 g of enone 2) was dissolved in 0.5% v/v sulfuric acid to make a 50 g/L solution. The substrate acid solution was pumped into the fermenter. The bioconversion was allowed to continue until completion (about 2–4 h).

Assay to Determine Bioconversion

Bioconversion samples were prepared as methanol dilutions (typically 10:1 MeOH to sample) or by extraction with one volume ethyl acetate followed by recovery and drying of the organic phase with resuspension to appropriate mobile phase for reverse phase quantitative analysis or normal phase chiral analysis.

Samples were analyzed by reverse-phase HPLC utilizing an Agilent Eclipse XDB C-18 column (15 cm length, 3.5 μm particle size) via a 1.0 mL/min gradient method from 30–60% acetonitrile. The mobile phase was adjusted to 13.5 mM phosphate and pH adjusted to 6.0. Product allylic alcohol 7 was observed as a distinct 255 nm peak with retention time of about 3.2 min which was effectively separated from substrate enone 2 (retention time of about 4.6 min). Bioconversion yield was calculated from integration of the area under the substrate and product peaks referenced to an appropriate series of allylic alcohol and enone standards.

Assay to Determine Enantiomeric Excess (ee)

Samples were analyzed by normal phase isocratic HPLC (30% hexane/70% ethanol +0.5% triethylamine) utilizing a Chiralpak AD (Chiral Technologies) column (25 cm length, 10 μm particle size). The 12-minute separation was run at 1.5 mL/min at 35° C. Desired (R)-allylic alcohol product 7 eluted first with a retention time of 5.6 min whereas (S)-allylic alcohol eluted with a retention time of 7.44 min. Enantiomeric excess (ee) was determined according to the standard convention: (Area R−Area S/(Area R+Area S))*100.

Isolation

Step 1: Whole Broth Extraction and Cell Removal—10% v/v MeOH was added to the broth which was then filtered to remove the product-rich supernatant. The supernatant was typically 85% of the whole broth volume. The cell pellet was then resuspended in one volume (equivalent to original supernatant) of 10% MeOH and washed for 1 h. The suspension was filtered to recover the water extract.

Step 2: Solid Phase Extraction—The extracts were loaded onto a resin column (Amberchrom CG-161 cd) at about 85 g of allylic alcohol per liter of resin. The resin was then flushed with two column volumes of water followed by two column volumes of 20:80 acetonitrile:water. The column was then eluted with 80:20 acetonitrile:water. Approximately 3 column volumes of eluent were needed to recover the product.

Step 3: Solvent Extraction—The column eluent was extracted using 1:1 volume isopropyl acetate (IPAc). After decanting the product-rich organic layer the aqueous layer was washed with an additional volume of IPAc.

Step 4: Solvent Switch—The extracts were then combined and distilled to reach a product concentration of approximately 16 g/L. The concentrate was then continuously distilled while IPAc was added to remove residual water to <0.5 vol %.

Step 5: Crystallization—The solution was distilled to reach a final concentration of about 100 g/L allylic alcohol 7. The (R)-allylic alcohol 7 was then precipitated by adding heptane (anti-solvent) to reach about 50% v/v in solution. The slurry was then cooled to 4° C. and aged for 1 h. The resulting slurry was filtered with the solids dried under vacuum at 40° C. The product was characterized by NMR and mass spectroscopic methods.

EXAMPLE 2

Reduction of Enone 8 Mediated by *Candida Chilensis* Strain MY1708

Step A: 1-(Pyrimidin-5-yl)-7-(5,6,7,8-tetrahydro-[1,8]naphthyridin-2-yl)-hept-1-en-3-one (8)

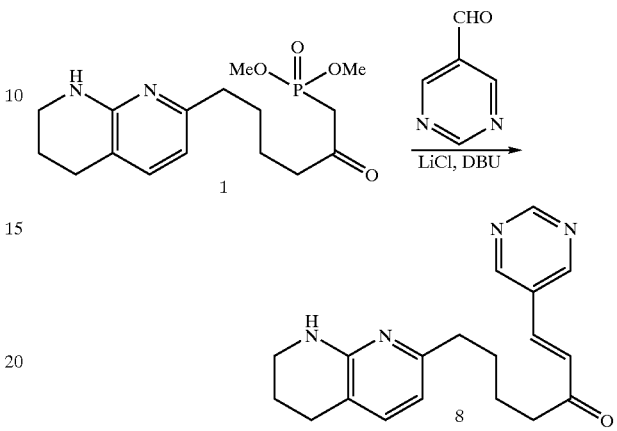

To a stirred suspension of anhydrous lithium chloride (3.54 g, 83.3 mmol) in acetonitrile (350 mL) at room temperature was added a solution of ketophosphonate 1 (for preparation of 1, see U.S. Pat. No. 6,048,861) (28.3 g, 83.1 mmol) in acetonitrile (128 mL). After stirring for 15 min, a solution of DBU (9.52 mL, 64.1 mmol) in acetonitrile (32 mL) was added to produce a mostly fine white precipitate with some larger masses. The reaction mixture was briefly sonicated to break up the larger masses and stirred for 30 min. A solution of pyrimidine-5-carboxaldehyde (6.92 g, 64.1 mmol) in acetonitrile (128 mL) was added over 15 min. After 2 h, the reaction mixture was filtered and the filtrate concentrated. The residue was purified by flash chromatography (8% MeOH/EtOAc) to give 18.5 g of enone 8 as a yellow crystalline solid; m.p. 101–102° C.

$^1$H NMR (400 MHz, CDCl$_3$): δ 9.19 (s, 1H), 8.89 (s, 2 H), 7.45 (d, J=16.3 Hz, 1H), 7.05 (d, J=7.3 Hz, 1H), 6.85 (d, J=16.3 Hz, 1H), 6.35 (d, J=7.3 Hz, 1H) 4.78 (br s, 1H), 3.39 (m, 2H), 2.72–2.67 (om, 4H), 2.58 (m, 2H), 1.89 (m, 2H), 1.79–1.72 (om, 4H) ppm.

$^{13}$C NMR (100 MHz, CDCl$_3$): δ 199.3, 159.40, 159.36, 158.0, 155.9, 136.8, 134.7, 129.4, 128.8, 113.5, 111.5, 41.8, 41.6, 37.7, 29.5, 26.5, 23.9, 21.7 ppm.

Step B: (R)-1-(Pyrimidin-5-yl)-7-(5,6,7,8-tetrahydro-[1,8]-naphthyridin-2-yl)-hept-1-en-3-ol (9)

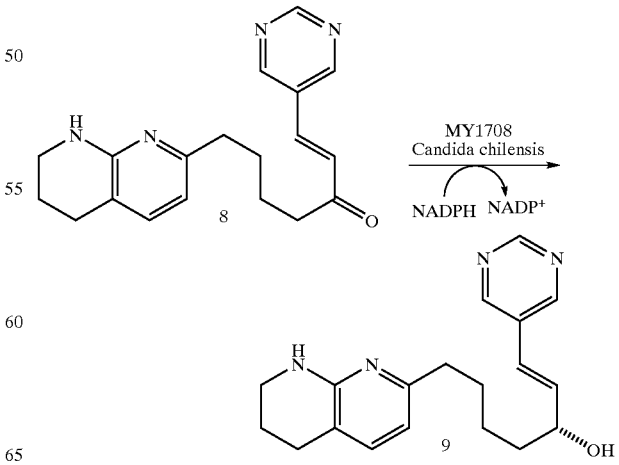

Enone substrate 8 was subjected to the bioreduction conditions of Example 1. The desired (R)-allylic alcohol 9 was isolated, crystallized, and characterized by NMR and mass spectroscopic methods. The bioconversion yield of 9 was 0.63 g/L. The ee of 9 was 90%. The amount of saturated ketone of structural formula VI (R=H) was 0.34 g/L, and the amount of saturated alcohol of structural formula V (R=H) was 0.22 g/L.

EXAMPLE 3
Reduction of Enone 8 Mediated by *Candida Chilensis* Strain MY1708 in the Presence of Added trans-Cinnamic Acid Enone substrate 8 was subjected to the bioreduction conditions as described below:

Bioreduction

Step 1: Cell growth—The yeast medium used for the fermentation process is shown in Table 1 above. The fermenter was sterilized (121° C. for 45 min) containing the potassium phosphate monobasic, sodium phosphate dibasic, magnesium sulfate heptahydrate, calcium carbonate, and monosodium glutamate, as well as trace elements. Glucose was added to the fermenter after separate sterilization. The vitamins were filter-sterilized to the post sterile fermenter. *Candida chilensis* yeast cells (MY1708) were inoculated into the fermenter at around 0.04–1% v/v from a frozen source. The temperature was maintained at 25° C. and the pH at 4.5 using 25% v/v sulfuric acid and 25% w/v sodium hydroxide. A glucose feed (2 g/Lh) was started when glucose consumption is near completion (20–30 h). The fermentation was completed at 30–50 hours.

Step 2: Bioreaction—For the bioconversion, the pH increased around 7.0 to 8.7 via addition of 25% w/v sodium hydroxide. This was followed by a glucose addition (2–50 g/L), trans-cinnamic acid (1.48–4 g/L) and finally the substrate 8. Trans-Cinnamic acid (222 g) was dissolved in DMSO to make a 222 g/L solution which was pumped to the fermenter. Alternatively, the cinnamic acid was added directly as a solid. 100 g of enone 8 was dissolved in 0.5% v/v sulfuric acid to make a 50 g/L solution. The substrate acid solution was pumped into the fermenter. The bioconversion was allowed to continue until completion (about 2–6 h).

Isolation

Step 1: Whole Broth Extraction and Cell Removal—10% v/v MeOH and 0.4 v/v triethylamine (TEA) relative to the total broth volume was added to the broth which was then filtered to remove the product-rich supernatant. TEA was added to prevent adsorption of cinnamic acid to the resin in the subsequent solid phase extraction step. The supernatant was typically 85% of the whole broth volume. The cell pellet was then resuspended in one volume (equivalent to original supernatant) of 89.6:10:0.4 water::MeOH:TEA and washed for 1 h. The suspension was filtered to recover the water extract.

Step 2: Solid Phase Extraction—The extracts were loaded onto a resin column (Amberchrom CG-161 cd) at about 85 g of allylic alcohol per liter of resin. The resin was then flushed with two column volumes of water followed by two column volumes of 20:80 acetonitrile:water. Before eluting the column was washed with an additional two column volumes of water. The column was then eluted with isopropyl alcohol (IPA). Approximately 3 column volumes of eluent were needed to recover the product.

Step 3: Solvent Switch—The column eluent was concentrated via distillation to reach a product concentration of approximately 200 g/L allylic alcohol 9. The solution was then continuously distilled while IPA was added to maintain a constant volume. This was continued until the water content was reduced to <0.5%, requiring approximately two concentrated batch volumes.

Step 4: Crystallization—The solution was distilled to reach a final concentration of about 200 g/L allylic alcohol 9. At this point, the solution was aged for 2 h to crystallize unreacted substrate. The slurry was then filtered with the mother liquors recovered (product rich). The (R)-allylic alcohol 9 was then precipitated by adding heptane (antisolvent) to reach about 50% v/v in solution. The slurry was then cooled to 4° C. and aged for 1 h. The resulting slurry was filtered with the solids dried under vacuum at 40° C. The product was characterized by NMR and mass spectroscopic methods. The bioconversion yield of 9 was 0.87 g/L, with 9 being formed with an ee of 98%. The amount of saturated ketone of structural formula VI (R=H) was 0.11 g/L, and the saturated alcohol of structural formula V (R=H) was 0.04 g/L.

Results obtained with other carboxylic acids of formula IV are provided in Table II. Results are given as HPLC area % amounts of allylic alcohol 9, the saturated alcohol V, and the saturated ketone VI formed in the bioreduction.

TABLE II

| Additive | 9 | % ee | Amount of V (R = H) | Amount of VI (R = H) |
|---|---|---|---|---|
| 4-phenyl-3-butenoic acid | 86.2 | 97.4 | 3.6 | 5.8 |
| α-phenyl-cinnamic acid | 75.6 | 96.8 | 1.9 | 15.4 |
| cis-2-methoxy-cinnamic acid | 76.3 | 96.0 | 7.8 | 10.7 |
| α-methyl-cinnamic acid | 84.6 | 97.6 | 3.7 | 6.6 |
| 3-(1-naphthyl)-acrylic acid | 78.5 | 95.5 | 6.3 | 9.0 |
| 3-(2-naphthyl)-acrylic acid | 81.4 | 97.4 | 3.6 | 9.0 |
| 4-aminocinnamic acid HCl (predominantly trans) | 65.2 | 95.6 | 9.3 | 19.1 |
| hydrocinnamic acid | 77.2 | 97.0 | 5.9 | 12 |
| crotonic acid | 66.6 | 97.7 | 1.54 | 24.3 |
| trans-cinnamic acid | 95.4 | 98.8 | 0.06 | 0.92 |
| control-water (average) | 47.5 | 89.8 | 3.27 | 33.4 |
| control-DMSO (average) | 48.8 | 89.9 | 5.33 | 33.2 |

What is claimed is:

1. A process for the preparation of a compound of structural formula I:

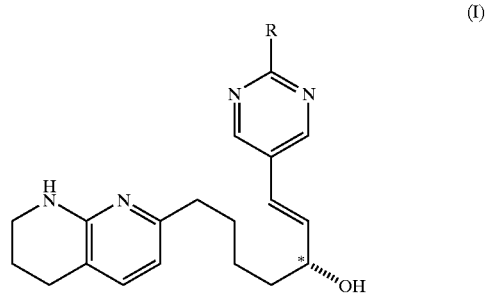

having the (R)-configuration at the stereogenic center marked with an *;

wherein R is hydrogen or methyl;

comprising the step of culturing a yeast microorganism selected from *Candida chilensis* strain MY1708 and

*Candid schatavii* strain MY1831 in a mixture comprising a propagation medium and an unsaturated ketone substrate of structural formula II:

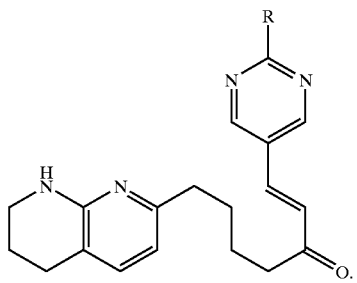
(II)

2. The process of claim 1 wherein the yeast microorganism is *Candida chilensis* strain MY1708.

3. The process of claim 1 wherein R is hydrogen.

4. The process of claim 1, wherein the mixture further comprises a carboxylic acid of structural formula IV:

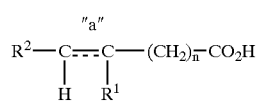
(IV)

wherein

"a" represents a single bond or a double bond;

n is 0, 1, or 2;

$R^1$ is hydrogen, phenyl, or methyl; and $R^2$ is $C_{1-4}$ alkyl or aryl wherein aryl is selected from the group consisting of phenyl, naphthyl, biphenyl, pyridyl, furanyl, thienyl, pyrrolyl, benzofuranyl, benzothiophenyl, and indoly, wherein the aryl group is unsubstituted or substituted with one to five substituents independently selected from halogen, amino, $C_{1-4}$ alkylamino, di-($C_{1-4}$ alkyl)amino, hydroxy, $C_{1-4}$ alkoxy, and $C_{1-4}$ alkyl.

5. The process of claim 4 wherein "a" represents a double bond, n is 0. $R^1$ is hydrogen, and $R^2$ is aryl.

6. The process of claim 5 wherein said carboxylic acid is cinnamic acid.

7. The process of claim 4 wherein said carboxylic acid is used in an amount of about 1 to about 50 molar equivalents of said unsaturated ketone substrate of structural formula II.

8. The process of claim 1 further comprising the step of isolating the compound of structural formula I from the propagation medium.

* * * * *